(12) United States Patent
Poncon

(10) Patent No.: US 10,159,794 B2
(45) Date of Patent: Dec. 25, 2018

(54) DRUG DELIVERY DEVICE AND ADAPTOR

(75) Inventor: Gilbert Poncon, Pommiers la Placette (FR)

(73) Assignee: Becton Dickinson France, Le Pont de Claix (FR)

( * ) Notice: Subject to any disclaimer, the term of this patent is extended or adjusted under 35 U.S.C. 154(b) by 640 days.

(21) Appl. No.: 14/232,744

(22) PCT Filed: Jul. 13, 2012

(86) PCT No.: PCT/EP2012/063827
§ 371 (c)(1),
(2), (4) Date: Jan. 14, 2014

(87) PCT Pub. No.: WO2013/010951
PCT Pub. Date: Jan. 24, 2013

(65) Prior Publication Data
US 2014/0171875 A1   Jun. 19, 2014

(30) Foreign Application Priority Data

Jul. 15, 2011   (EP) ..................... 11305927

(51) Int. Cl.
*A61M 5/31* (2006.01)
*A61M 5/34* (2006.01)
*A61M 39/10* (2006.01)

(52) U.S. Cl.
CPC .............. *A61M 5/31* (2013.01); *A61M 5/344* (2013.01); *A61M 5/345* (2013.01); *A61M 5/347* (2013.01); *A61M 5/348* (2013.01); *A61M 39/1011* (2013.01); *A61M 2039/1077* (2013.01)

(58) Field of Classification Search
CPC ............ A61M 2039/1077; A61M 5/31; A61M 5/344; A61M 5/345; A61M 5/347; A61M 39/1011; A61M 5/348; A61M 2039/1016; A61M 2039/1027; A61M 2039/1033; A61M 2039/1038; A61M 2039/1044; A61M 2039/1066; F16L 37/22
See application file for complete search history.

(56) References Cited

U.S. PATENT DOCUMENTS

| 4,198,080 | A | * | 4/1980 | Carpenter | .......... A61M 39/1011 24/635 |
|---|---|---|---|---|---|
| 4,369,781 | A | * | 1/1983 | Gilson | .................. A61M 5/346 285/332 |
| 4,540,405 | A | * | 9/1985 | Miller et al. | .................. 604/232 |
| 4,607,868 | A | | 8/1986 | Harvey et al. | |
| 5,489,125 | A | * | 2/1996 | Hohmann | ............. F16L 37/138 285/308 |
| 6,152,913 | A | * | 11/2000 | Feith et al. | .................... 604/533 |

(Continued)

*Primary Examiner* — Amber Stiles
(74) *Attorney, Agent, or Firm* — The Webb Law Firm

(57) ABSTRACT

Provided is a drug delivery device including: a reservoir for a product, having a distally projecting end-piece defining an axial passageway for the transfer of the product, with a distal portion, an adaptor having a collar engageable around said end-piece said collar being axially movable with respect to said end-piece, securing structure for limiting the axial movement of said collar with respect to said end-piece, between a most distal position and a most proximal position of said collar, and biasing element for urging said collar towards its most distal position. An adaptor for forming a drug delivery device is also provided.

19 Claims, 8 Drawing Sheets

(56) References Cited

U.S. PATENT DOCUMENTS

| | | | |
|---|---|---|---|
| 2006/0106349 A1* | 5/2006 | Kito | A61M 5/344 604/187 |
| 2008/0132851 A1* | 6/2008 | Shaw | A61M 5/347 604/199 |
| 2013/0046287 A1* | 2/2013 | Davis | A61M 39/10 604/535 |

* cited by examiner

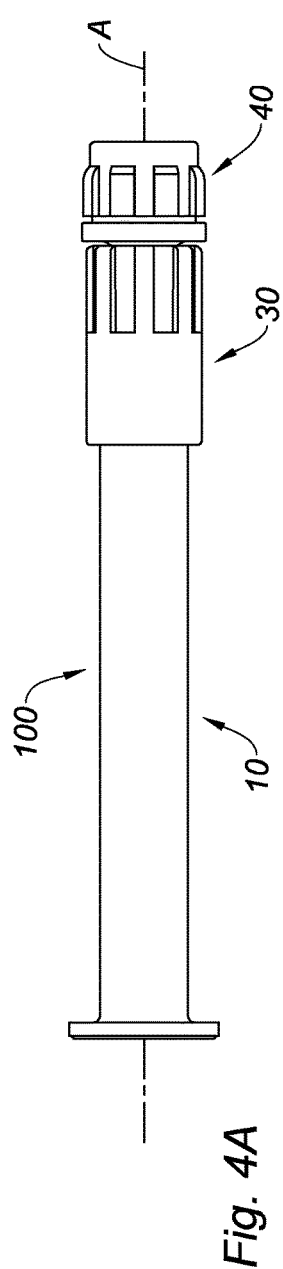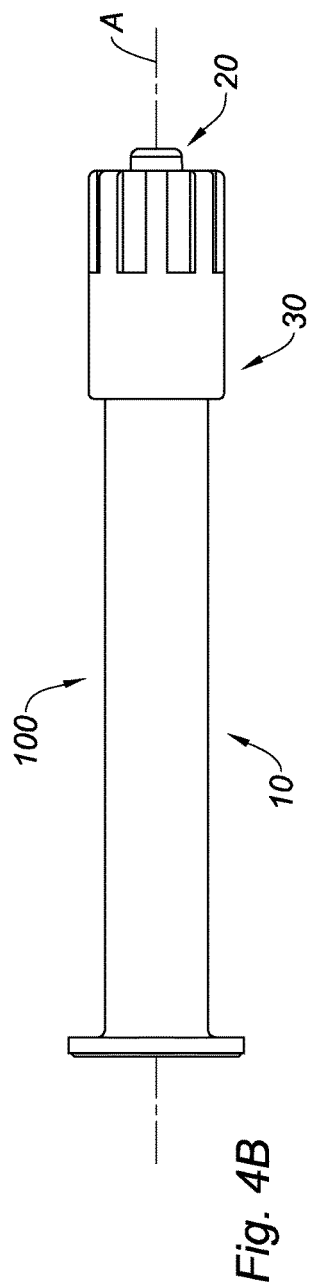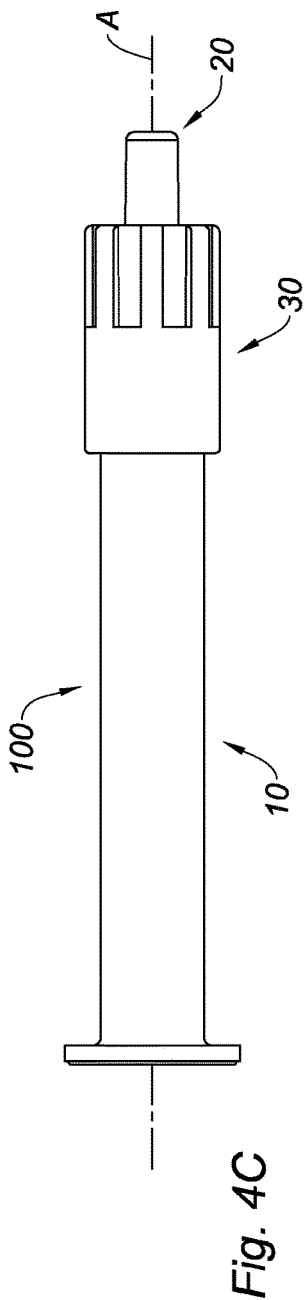
Fig. 4A
Fig. 4B
Fig. 4C

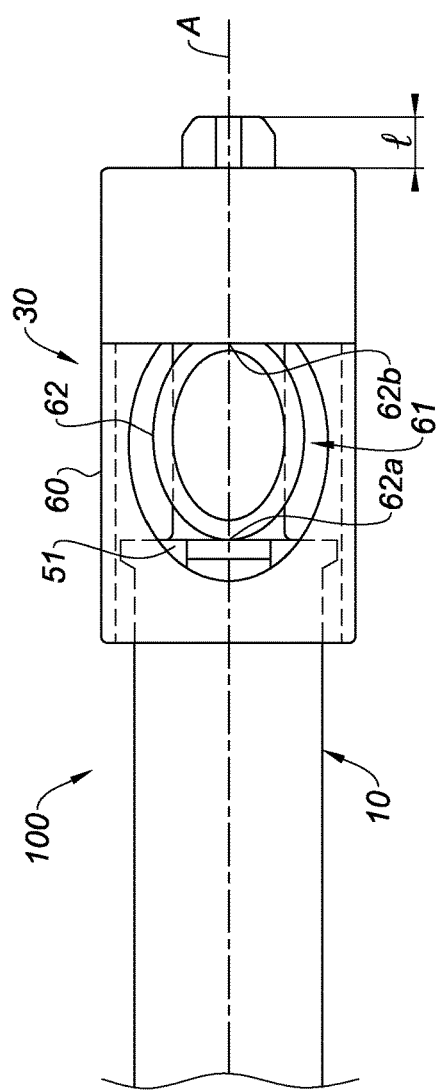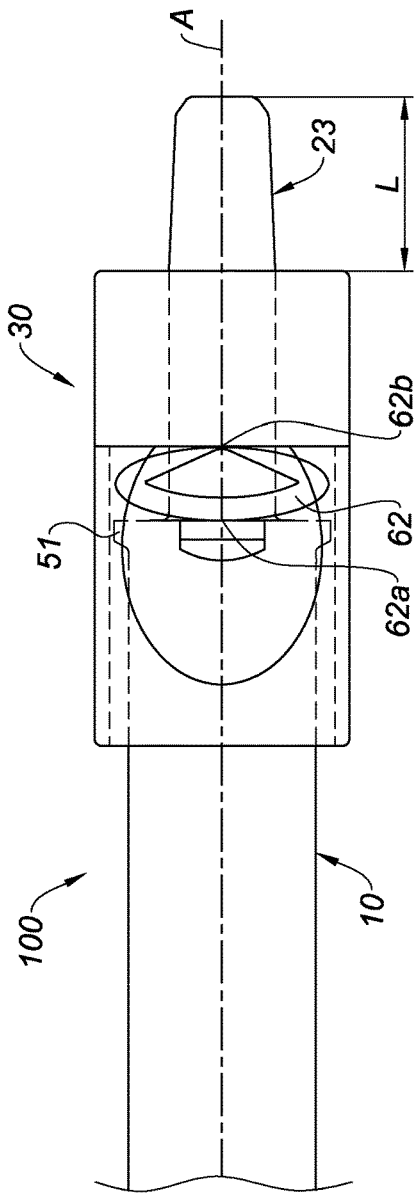
Fig. 7A
Fig. 7B

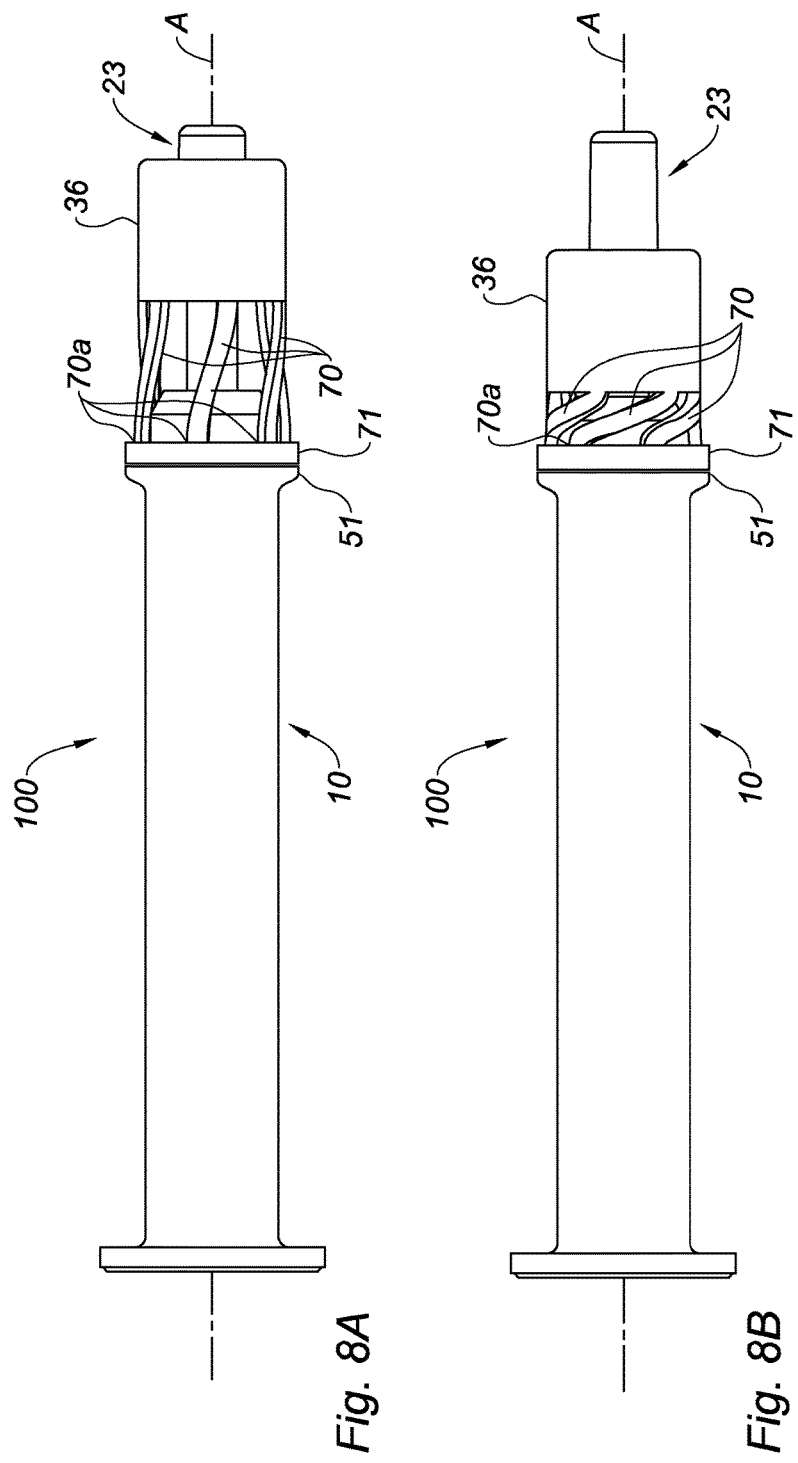

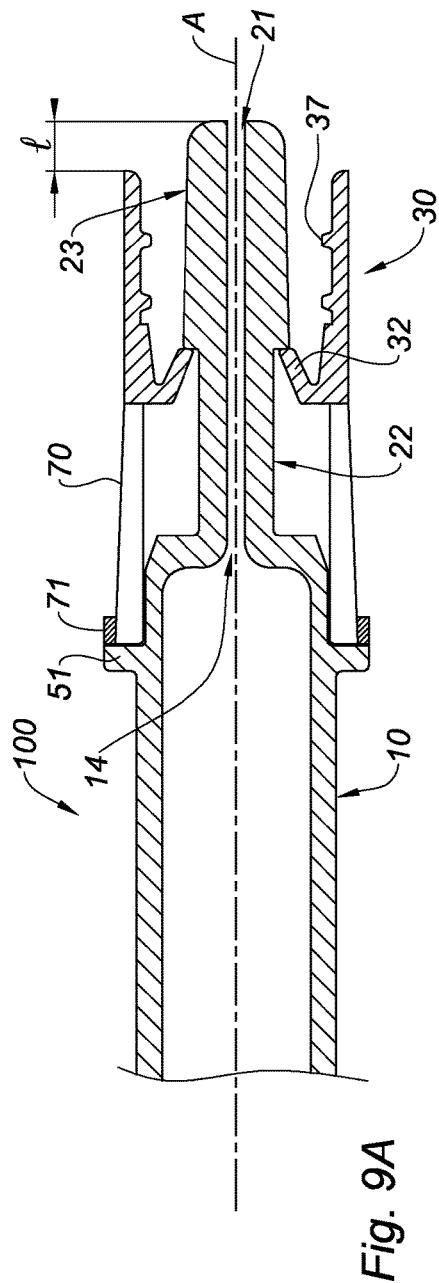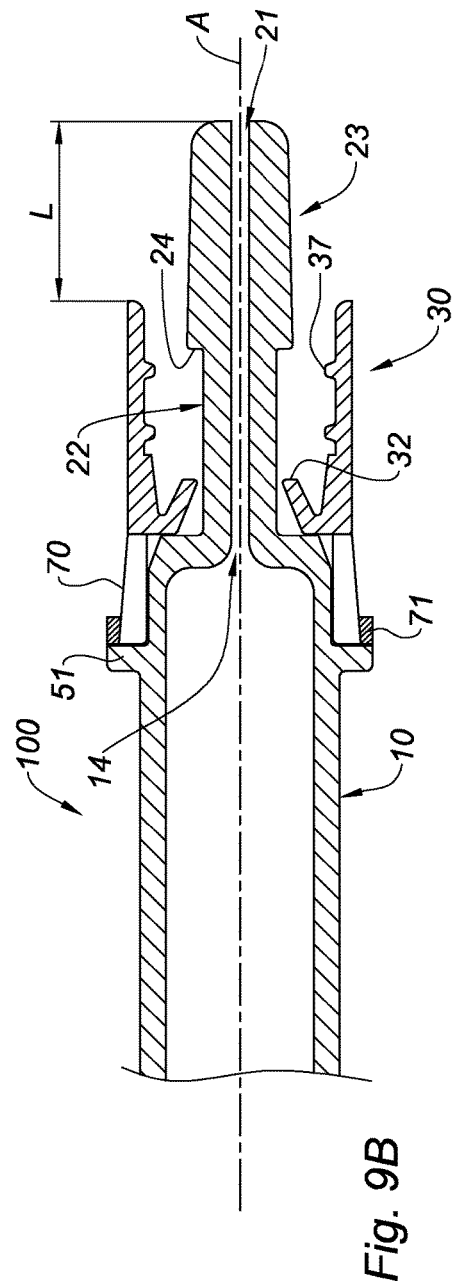

DRUG DELIVERY DEVICE AND ADAPTOR

BACKGROUND OF THE INVENTION

Field of the Invention

The present invention relates to a drug delivery device and an adaptor for, or intended to be used with said drug delivery device. The drug delivery device is provided with an end-piece around which the adaptor is engageable so as to enable the safe connection of a connector on said end-piece.

Description of the Related Art

Drug delivery devices usually comprise a hollow body forming a reservoir for containing a medical product. In addition, the distal end of the body forming the reservoir usually comprises an end-piece in which an axial passageway is arranged through which the said product is ejected from the reservoir.

In this disclosure, the distal end of a component or of a device must be understood as meaning the end furthest from the hand of the user and the proximal end must be understood as meaning the end closest to the hand of the user. Similarly, in this disclosure, the distal direction must be understood as the direction of injection or transfer of the product (i.e. from the reservoir to the Intra Veinous line) and the proximal direction is the opposite direction.

The handling of products, such as liquid medicine, in particular for a parenteral administration to a patient which is carried out via a perfusion device, as often in hospitals or in emergency situations, implies, in a general manner, the use of connectors, such as IV (Intra Veinous) connectors which link the drug delivery device, containing the product to be delivered, to the vein of the patient, usually via an IV line. Of course, the drug delivery device, in particular its end-piece and the connector must be assembled together correctly and securely.

Actually, there are different connection systems for connecting a connector to the end-piece of a drug delivery device, when the distal portion of said end-piece has the global shape of a distally tapered cone, also called a male Luer, as is usually the case.

In such cases, the male luer of the end-piece forming the male part of the connection system, the connector usually comprises a corresponding conical bore forming the female part of the connection system, also called a female luer, and intended to be fitted on the male luer in order to complete the connection.

In some cases, no additional element is provided on the connector, and the female luer is directly fitted on the male luer of the end-piece of the drug delivery device by simple force fitting: the connector is then called a luer slip connector and the connection is called a luer slip connection.

Alternatively, the connection system may comprise in addition an adaptor, said adaptor being fixed to the end-piece of the drug delivery device via a collar, and comprising a tubular wall at least partially surrounding the male luer of the end-piece. The tubular wall is provided with an inner thread intended to cooperate with a corresponding outer thread located on an outer wall of the connector provided with the female luer. In such a case, at the time of forming the connection, the female luer is fitted onto the male luer by means of threading the connector in the adaptor: the safe connection of the male luer and female luer is therefore improved. Such an adaptor is called a luer Lock Adaptor, the connector is called a luer Lock connector and the connection thus realized is called a luer lock connection. Alternatively, the threads may be replaced by cooperating wings.

It derives from these two connection systems that all the connectors may not have the same shapes: the connectors to be used for a luer Lock connection will comprise an outer thread (or a wing), whereas the connectors to be used for a luer slip connection will not. Indeed, if a luer slip connector is brought close to the distal portion of the end-piece of a drug delivery device provided with a luer Lock adaptor as described above, the luer Lock adaptor will be an obstacle to the female luer of the luer slip connector and will prevent the completion of a safe connection between the drug delivery device and the connector.

SUMMARY OF THE INVENTION

One aspect of the invention is to provide an adaptor engageable with the end-piece of a drug delivery device, in particular where the end-piece has a distal portion having a distally tapered cone shape such as a male luer, said adaptor being capable of easily changing positions so as to allow both types of connections, luer slip and luer lock, as described above, depending on which type of connector is provided, with no particular effort from the user. In particular, one aspect of the invention is to provide an adaptor engageable on the end-piece of a drug delivery device and allowing successive connections of various connector types, in particular luer lock and luer slip types, with no need for the user to reconfigure the drug delivery device between two connections, regardless of the type of the selected connector. With such an adaptor, the connection is completed whatever the connectors used with no additional action required from the user. The user just has to position the connector to the end-piece of the drug delivery device and the connection, either luer lock or luer slip, is automatically completed due to the possibility of the adaptor to adopt different configurations.

Another aspect of the invention is to provide an adaptor capable of coming back to its initial position after removal of the connector.

An aspect of the invention is a drug delivery device comprising:

a reservoir for containing a product, said reservoir having a distally projecting end-piece having a longitudinal axis and defining an axial passageway for the transfer of the product from the reservoir, said end-piece having a distal portion, an adaptor having a collar engageable around said end-piece so that said collar is axially movable with respect to said end-piece, securing means for limiting the axial movement of said collar with respect to said end-piece once said collar is engaged around said end-piece, between a most distal position of said collar, in which a first length of said distal portion is left uncovered by said adaptor, and a most proximal position of said collar, in which a second length of said distal portion, greater than said first portion, is left uncovered by said adaptor, biasing means for urging said collar towards its most distal position.

As will be clear from the following description, the collar of the adaptor of the drug delivery device of the invention is easily movable along the end-piece between its most proximal position, in which the length of the distal portion of the end-piece, in particular a male luer, left uncovered, in other words the second length, allows a luer slip connection to be completed, and its most distal position, in which the length of the distal portion left uncovered, in other words the first length, allows the adaptor to cooperate with the luer Lock connector in order to complete a luer lock connection. Indeed, when the collar is in its most proximal position, the length of the distal portion of the end-piece that is left uncovered allows a luer slip connector to be easily fitted on said distal portion, the adaptor forming no obstacle to this connection: the user needs only apply a proximal pressure to the biasing means, so as to put them in a stressed state, thereby pushing the collar in its proximal position, in order to connect the luer slip connector onto the distal portion of the end-piece.

Alternatively, if a luer lock connection is needed, the user does not need to apply a proximal pressure on the adaptor, as the presence of the biasing means automatically maintain the collar of the adaptor in its most distal position. The luer lock connection can therefore be simply completed by simply connecting the luer Lock connector to the adaptor, for example by threading, thereby completing a safe connection between the female luer and the distal portion of the end-piece.

In addition, thanks to the drug delivery device and adaptor of the invention, a user can simply change connectors without having to reconfigure the drug delivery device between two connections, regardless of the type of connector used. For example, if a luer slip connector is connected on the distal portion of the end-piece of the drug delivery device of the invention and the user wishes to replace it by a luer Lock connector, he simply needs to remove the luer slip connector. Thanks to the biasing means of the drug delivery device of the invention, the collar will automatically come back to its most distal position when the luer slip connector is removed, and the user may simply connect the luer Lock connector to the adaptor.

In embodiments, said securing means comprises proximal locking means for preventing said collar from moving beyond its most proximal position and distal locking means for preventing said collar from moving beyond its most distal position. For example, said proximal locking means comprise a transversal wall of said reservoir. The distal locking means may comprise an annular ridge provided on an outer wall of said end-piece and an abutment surface provided on an inner wall of said collar, said abutment surface coming in engagement onto said annular ridge when said collar is urged in the distal direction once it is engaged around said end-piece.

In embodiments, said biasing means comprise one or more flexible legs extending from said collar in the proximal direction, said flexible legs being in a first stressed state when said collar is in its most proximal position, said flexible legs being in a second stressed state when said collar is in its most distal position, said second stressed state being a state of lower stress than said first stressed state. In embodiments, the stress applied to the flexible legs in their second stressed state may tend to zero.

In embodiments, the drug delivery device may further comprise protection means for preventing access to the biasing means by a user. For example, said protection means comprise a proximal tubular wall extending from said collar in the proximal direction and surrounding said flexible legs. Such a proximal tubular wall prevents that the biasing means, for example the flexible legs, be damaged.

In embodiments, the drug delivery device comprises anti-rotation means for limiting the rotation of said collar with respect to the end-piece once said collar is engaged with said end-piece. Said anti-rotation means may comprise one or more longitudinal ridge located on an outer wall of said end-piece, and one or more recess located on an inner wall of said collar, said longitudinal ridge being engaged into said recess and thereby preventing said collar to rotate with respect to said end-piece. Such anti-rotation means allow a safe threading of the luer Lock connector into the adaptor, as the adaptor is maintained locked in rotation with respect to the end-piece when the luer Lock connector is threaded therein.

In embodiments, the adaptor further comprises a distal tubular wall extending from said collar in the distal direction and surrounding at least part of said distal portion of said end-piece when said collar is engaged around said end-piece, said tubular wall being provided on its inner wall with a thread. Said thread is preferably arranged so as to cooperate with the complementary thread located on a luer lock connector to be connected to the end-piece of the reservoir.

In embodiments, said flexible legs are made of a material selected from olefins, polyimide, polycarbonate, polyetherketone and combinations thereof.

In embodiments, said end-piece is made of glass. Alternatively, said end-piece may be made of plastic.

In embodiments, said distal portion is a male luer, in other words is a distally tapered cone.

Another aspect of the present invention is an adaptor as described above, having a collar arranged for cooperating with a reservoir having a distally projecting end-piece having a longitudinal axis and defining an axial passageway for the transfer of the product from the reservoir, for forming a drug delivery device as described herein.

BRIEF DESCRIPTION OF THE DRAWINGS

The drug delivery device and adaptor of the invention will now be further described in reference to the following description and attached drawings in which:

FIGS. 7A and 7B are partial side views of another embodiment of the drug delivery device of the invention, in a luer lock connection position, and in a luer slip connection position, FIGS. 8A and 8B are side views of another embodiment of the drug delivery device of the invention, in a luer lock connection position, and in a luer slip connection position, and FIGS. 9A and 9B are cross section views of the drug delivery device of FIGS. 8A and 8B, in a luer lock connection position, and in a luer slip connection position.

DETAILED DESCRIPTION

Figure 1:
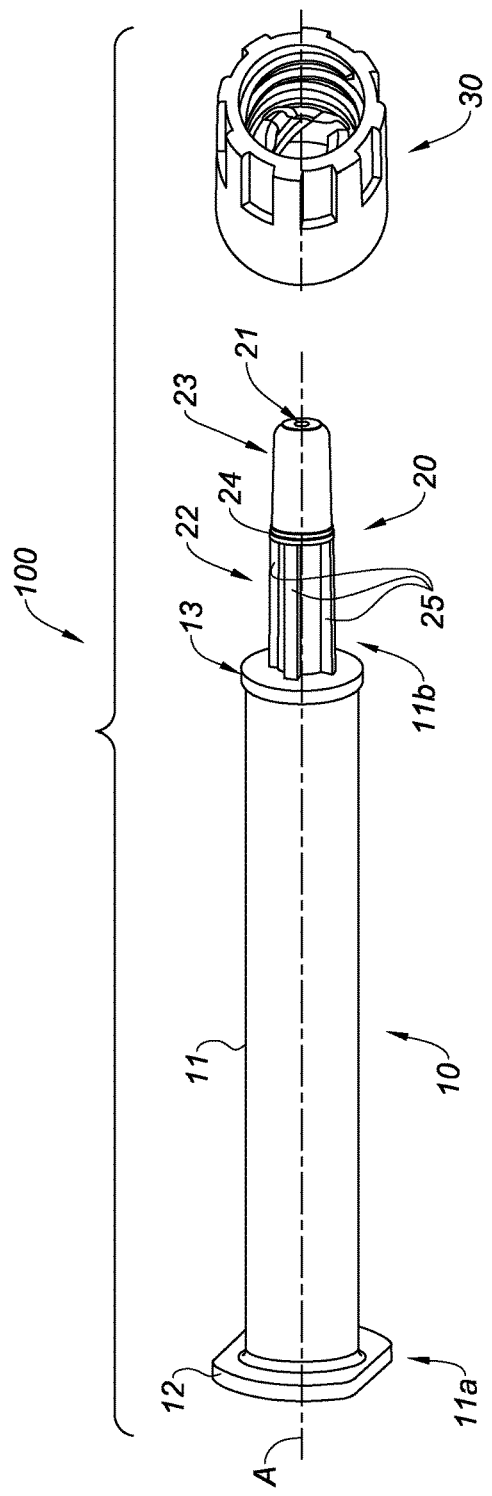
FIG. 1 is a perspective view of a drug delivery device of the invention, before engagement of the adaptor onto the end-piece of the drug delivery device.

With reference to FIG. 1 is shown a drug delivery device 100 of the invention comprising a reservoir 10 having a distally projecting end-piece 20 and an adaptor 30 intended to be engaged onto the end-piece 20. As appears from this figure, all the elements of the drug delivery device 1, in other words the reservoir 10, the end-piece 20 and the adaptor 30, are aligned along a longitudinal axis A.

The reservoir 10 is intended to contain a product to be delivered to a patient. The reservoir 10 may be formed of any material suitable for storing a product such as a medicine or drug. It may be made out of glass or plastic materials. On the example shown, the reservoir 10 has the global shape of a syringe body and comprises a tubular barrel 11, open at its proximal end 11a where it is provided with an outer flange 12 intended to form a pushing surface for the user at the time of delivery of the product to a patient.

At its distal end 11b, the tubular barrel 11 is substantially closed by a transversal wall 13, except for a central opening 14 (see FIG. 5B) for the passage of the product towards the end-piece 20.

Figure 5A:
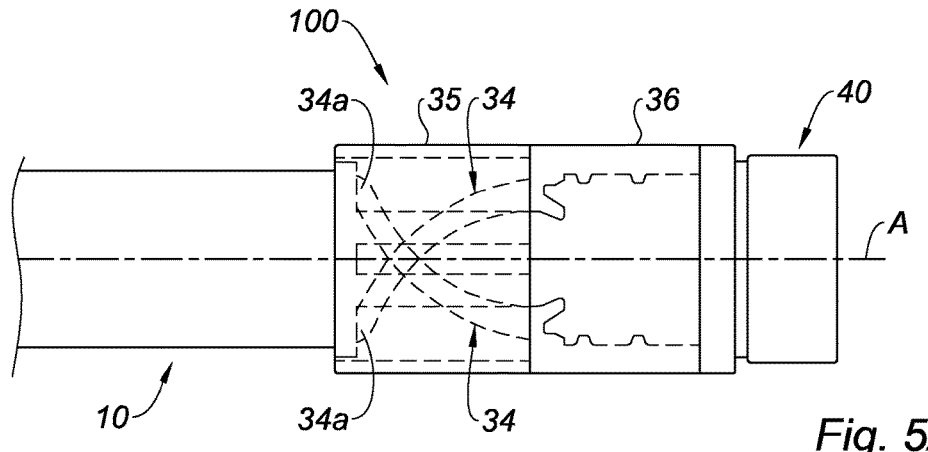
FIGS. 5A to 5C are cross section views of the drug delivery device of FIG. 1 corresponding to the positions shown on FIGS. 4A to 4C, FIGS. 6A and 6B are partial side views of another embodiment of the drug delivery device of the invention, in a luer lock connection position, and in a luer slip connection position.
Figure 5B:
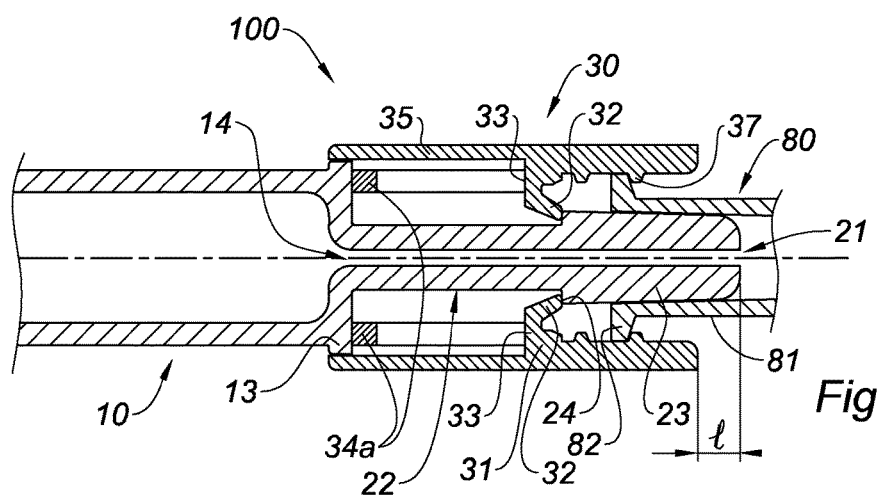
Figure 5C:
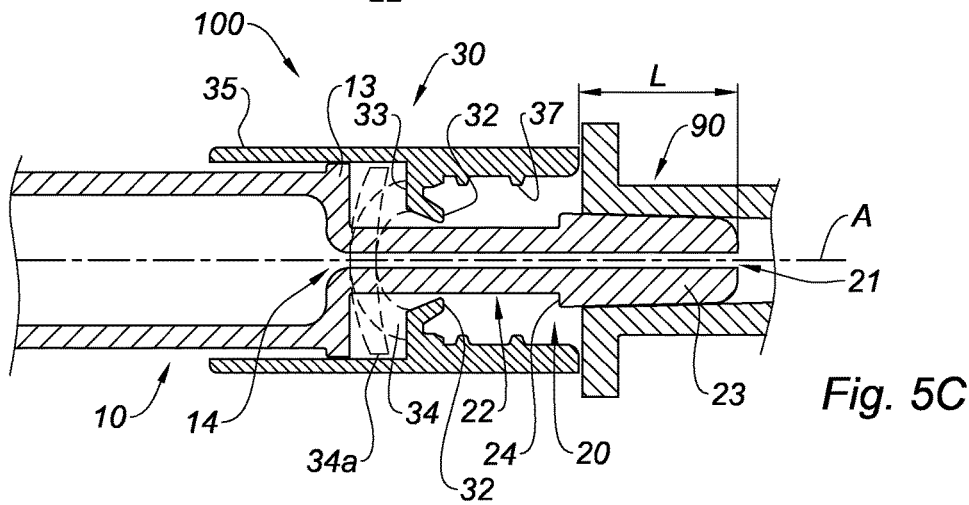

With reference to FIGS. 1 and 5B-C, the reservoir 10 is further provided with a distally projecting end-piece 20, extending from the transversal wall 13, aligned on longitudinal axis A and defining an axial passageway 21 (see FIGS. 5B and 5C) for the transfer of the product (not shown) from the reservoir 10 to the outside, in particular to a connector (partially shown on FIGS. 5B and 5C).

With reference to FIGS. 1 and 5B and 5C, the end-piece 20 is provided with a proximal portion 22, extending distally from the transversal wall 13 and having a tubular shape showing a constant outer diameter. The end-piece 20 is further provided with a distal portion 23, extending from the distal end of the proximal portion 22, and having a distally tapered conical shape, also called a male luer. In addition, the outer diameter of the proximal end of the distal portion 23 being greater than the outer diameter of the proximal portion 22, a distal abutment surface 24 is formed at the junction between the proximal portion 22 and the distal portion 23 of the end-piece 20.

As appears from FIG. 1, the proximal portion 22 of the end-piece 20 is further provided on its outer wall with four (only three are visible on FIG. 1) longitudinal ridges 25 regularly distributed along a circumference of the proximal portion 22.

With reference to FIGS. 1-3 and 5A-5C, the adaptor 30 will now be described in detail. The adaptor 30 comprises a collar 31 capable of being engaged around, and in contact with, the outer wall of the end-piece 20. The collar 31 comprises a annular transversal wall 33 provided with radial flexible tabs 32 capable of outwardly deflecting when the collar 31 is mounted on the distal portion 23 of the end-piece 20 and of coming back to a lower stressed state or even to their rest state, as shown on FIGS. 2, 3 and 5B, once the collar 31 is engaged around the proximal portion 22 of the end-piece 20. In its position where it is engaged around the proximal portion 22 of the end-piece, the collar 31 is axially movable along the length of the proximal portion 22. On the example shown, the collar 31 has four radial flexible tabs 32, regularly distributed along the circumference of the collar 31, only two of which are visible on the figures. The interspaces between these four radial flexible tabs 32 define four radial recesses 38, only three of them are at least partially visible on FIG. 3.

Figure 3:
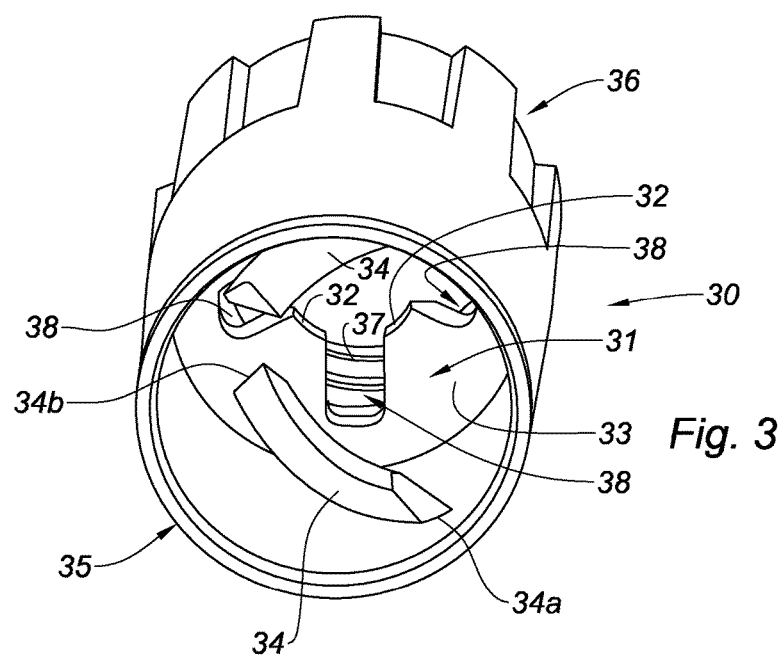
FIG. 3 is a bottom perspective view of the adaptor of FIG. 1, FIGS. 4A to 4C are side views of the drug delivery device of FIG. 1 in a storage position, in a luer lock connection position, and in a luer slip connection position.

As shown on FIG. 3, the adaptor 30 further comprises two helicoidal flexible legs 34, diametrically opposed from each other, and extending from a proximal face of the annular transversal wall 33 of the collar 31 in the proximal direction: the distal ends 34b of the helicoidal flexible legs 34 are therefore fixed to the annular transversal wall 33 while their proximal ends 34a are free. The flexible legs 34 are made of a material allowing them to be deflected under a stress and to come back to a lower stressed state or to a rest state, when the stress is released. As will appear from the description below, the flexible legs 34 are in a first stressed state when the collar 31 is in its most proximal position, the flexible legs being in a second stressed state when the collar 31 is in its most distal position, said second stressed state being a state of lower stress than said first stressed state. For example, the flexible legs may be made of a material selected from olefins, polyamide, polycarbonate, polyetherketone and combinations thereof.

With reference to FIG. 3, the adaptor 30 is further provided with a proximal tubular wall 35 extending from the collar 31 in the proximal direction and surrounding the helicoidal flexible legs 34. As will appear from the description below, such a proximal tubular wall 35 protects the helicoidal flexible legs as it prevents them from being reached by a user and/or from being damaged during storage of the drug delivery device for example.

Figure 2:
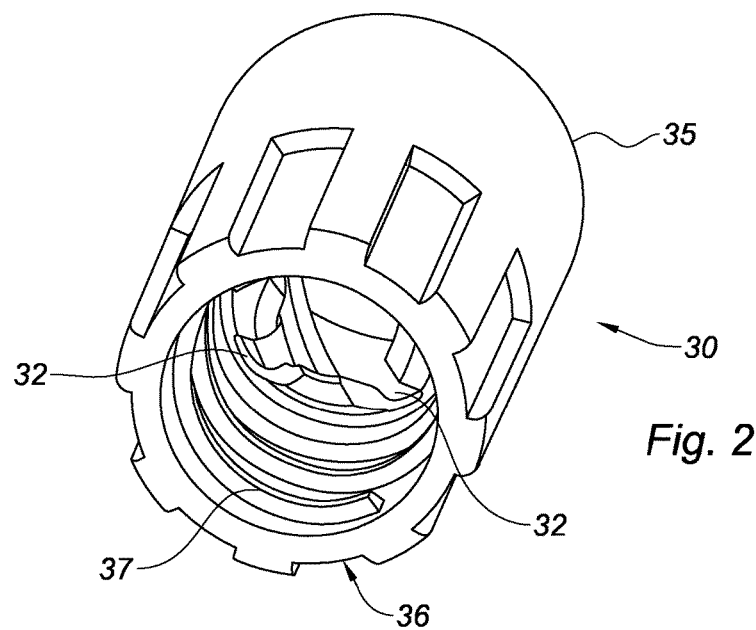
FIG. 2 is a top perspective view of the adaptor of FIG. 1.

With reference to FIG. 2, the adaptor 30 is further provided with a distal tubular wall 36, extending from the collar 31 in the distal direction. The inner wall of the distal tubular wall is provided with a thread 37, the function of which will be explained later.

The operation of the adaptor 30 and the drug delivery device 100 will now be explained with reference to FIGS. 1-5C. In order to be operational, the adaptor 30 is engaged onto the end-piece 20 of the reservoir 10. To this purpose, the proximal end of the adaptor 30 is approached from the distal end of the end-piece 20: thanks to the capability of the radial flexible tabs 32 to deflect outwardly, the collar 31 is force-fitted onto the distal portion 23 of the end-piece 20 and pushed in the proximal direction until it reaches the outer wall of the proximal portion 22, around which it is fitted: in this position of the adaptor 30, the radial flexible tabs 32 come back to their rest state and may be in contact with the outer wall of the proximal portion 22 so as to let the collar 31 capable of moving in translation along the length of the proximal portion 22.

In the second stressed state of the helicoidal flexible legs 34, i.e. in their state of lower stress, the collar 31 is in a most distal position, as shown on FIG. 5B: the helicoidal flexible legs 34 therefore act as biasing means for urging the collar 31 in its most distal position: in this position, the distal ends of the radial flexible tabs 32 come in distal abutment against the distal abutment surface 24 formed at the junction between the proximal portion 22 and the distal portion 23 of the end-piece 20, thereby preventing the collar 31 to move further distally. The radial flexible tabs 32 and the distal abutment surface 24 therefore form distal locking means of securing means for limiting the axial movement of the collar in the distal direction.

As shown on FIGS. 4A and 5A, the drug delivery device 100 may be provided to the user with a cap 40 closing the distal end of the drug delivery device 100. Once the cap 40 has been removed, the drug delivery device 100 may be used. The drug delivery device 100 is therefore in a use position, as shown on FIGS. 4B and 5B, with the collar 31 of the adaptor 30 in its most distal position.

In this position as shown on FIG. 5B, the drug delivery device 100 is capable of being connected to a luer lock connector 80 (partially shown), i.e. provided with a conical bore 81, for example a female luer, intended to be fitted on the distal portion 23 (corresponding to a male luer) of the end-piece 20, said conical bore 81 bearing in addition an outer thread 82 capable of cooperating with the thread 37 of the inner wall of the distal tubular wall 36 of the adaptor 30 of the drug delivery device of the invention. The drug delivery device 100 is therefore in a luer lock connection position. The user has therefore no additional step to perform in order to complete a luer lock connection with a luer lock connector, other than threading the luer Lock connector 80 into the thread 37 of the adaptor 30: thanks to the four longitudinal ridges 25 of the proximal portion 22 being engaged in the four radial recesses 38 of the adaptor 30, and acting as anti-rotation means, the adaptor remains locked in rotation with respect to the end-piece, when the luer Lock connector is threaded thereon. The luer Lock connection is therefore safely completed.

In the luer Lock connection position of the drug delivery device as shown on FIG. 5B, the length of the distal portion 23 which is left uncovered by the distal tubular wall 36, represented by the letter "l" on FIG. 5B, is not sufficient to allow the connection of a luer slip connector.

Nevertheless, thanks to the adaptor 30 of the invention, if the user wishes to perform a luer slip connection, he just needs to push the adaptor 30 in the proximal direction, for example by the intermediate of a luer slip connector 90 as shown on FIG. 5C: thanks to the capability of the helicoidal flexible legs 34 to deflect, the collar 31 moves in the proximal direction until it reaches its most proximal position, as shown on FIGS. 4C and 5C. In this position, the collar 31 comes in abutment against the transversal wall 13 by the intermediate of the helicoidal legs 34 which reach their stressed state. The transversal wall 13 therefore forms proximal locking means of securing means for limiting the axial movement of the collar 31 in the proximal direction.

As shown on FIG. 5C, the length now left uncovered by the distal tubular wall 36 of the adaptor 30, represented by the letter "L" on FIG. 5C, is greater than the first length "l" of FIG. 5B, and is sufficient for allowing the luer slip connector 90 to be safely connected on the distal portion 23 of the end-piece 20 of the drug delivery device 100.

Moreover, thanks to the helicoidal flexible legs forming biasing means for urging the collar 31 in its most distal position, the drug delivery device 100 may come back in its luer lock connection position easily, as soon as the user removes the luer slip connector 90 and releases the proximal pressure he exerts on the adaptor 30. The drug delivery device 100 of the invention is therefore particularly easy to use and to reuse subsequently for any type of connector. For instance, in a case where the reservoir is to be connected successively to more than one connector, for example because successive portions of the product contained in the reservoir are to be transferred to various lines or patients, the user has no additional step to perform on the drug delivery device in order to replace a luer slip connector by a luer lock connector: if a luer slip connector was connected to the end-piece 20 in the first place and the drug delivery device 100 was in its luer slip connection position as shown on FIG. 5C, then, the removal of the luer slip connector by the user automatically places the drug delivery device 100 in its luer lock connection position as shown on FIG. 5B, thanks to the helicoidal flexible legs 34 acting as biasing means for moving back the collar 31 in its most distal position. The user may then, as already described, connect easily a new connector, either a luer lock connector or a luer slip connector.

The drug delivery device of the invention and its adaptor therefore allow quick, simple, and numerous changes of connectors, regardless of the types of these connectors. It allows safe connections and allows time-saving.

Figure 6A:
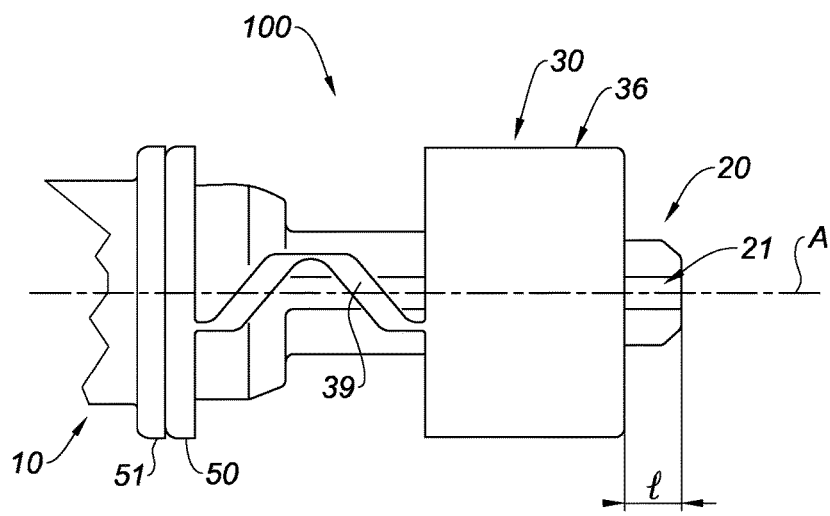
Figure 6B:
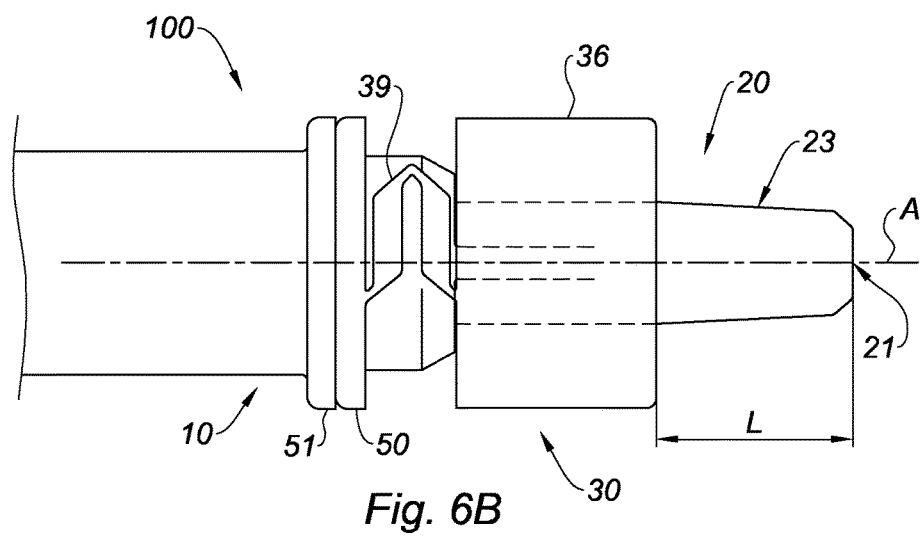

With reference to FIGS. 6A and 6B, is shown another embodiment of an adaptor 30 of the drug delivery device 100 of the invention. The references designating the same elements as in FIGS. 1-5C have been maintained; however the connectors, either luer Lock connector or luer slip connector, have been omitted. In this embodiment, no proximal tubular wall is provided and the helicoidal flexible legs are replaced by bending legs 39: for example the biasing means may comprise two diametrically opposed bending legs 39, only one of which is visible on FIGS. 6A and 6B. The proximal end of the bending legs 39 is fixed to an annular proximal wall 50 bearing on an outer transversal flange 51 replacing the transversal wall 13 of embodiments of FIGS. 1-5C. The drug delivery device 100 and adaptor 30 of FIGS. 6A and 6B function in the same manner as that of FIGS. 1-5C.

On FIG. 6A, the drug delivery device 100 is in its luer lock connection position, and therefore may be connected to a luer lock connector (not shown). On FIG. 6B, the adaptor 30 has been pushed in the proximal direction thanks to the capability of the bending legs 39 to bend and collapse, and the drug delivery device 100 is in its luer slip connection position, the length L of the distal portion 23 of the end-piece 20 that is left uncovered being sufficient to accept the conical bore, or female luer, of a luer slip connector (not shown).

In addition, thanks to the biasing properties of the bending legs 39, the drug delivery device 100 is capable of coming back automatically to its luer lock connection position, as soon as the proximal pressure exerted on the adaptor is released, for example, when the luer slip connector is removed in view of changing connectors.

With reference to FIGS. 7A and 7B, is shown another embodiment of an adaptor 30 of the drug delivery device 100 of the invention. The references designating the same elements as in FIGS. 1-5C have been maintained; however the connectors, either luer Lock connector or luer slip connector, have been omitted. In this embodiment, no proximal tubular wall is provided and the helicoidal flexible legs are replaced by a sleeve 60 provided with a window 61, a distal edge of which is provided with a longitudinally collapsible oval ring 62 having elastic properties. The distal end 62b of the oval ring 62 is fixed to the distal edge of the window 61, while the proximal end 62a of the oval ring 62 is free. In the rest state of the oval ring 62, as shown on FIG. 7A, the drug delivery device 100 is in its luer lock connection position. In the collapsed state of the oval ring 62, also a stressed state of said oval ring 62, as shown on FIG. 7B, the drug delivery device 100 is in its luer slip connection position: in such a state, the free proximal end 62a of the oval ring is in abutment against the outer transversal flange 51 of the reservoir 10. Thanks to the elastic properties of the oval ring 62, the drug delivery device 100 is automatically moved back in its luer lock connection position when the proximal pressure exerted on the adaptor 30 is released.

With reference to FIGS. 8A to 9B, is shown another embodiment of an adaptor 30 of the drug delivery device 100 of the invention. The references designating the same elements as in FIGS. 1-5C have been maintained; however the connectors, either luer Lock connector or luer slip connector, have been omitted. In this embodiment, no proximal tubular wall is provided and the two helicoidal flexible legs are replaced by a plurality of collapsible legs 70, the proximal ends 70a of which are all linked to an annular proximal wall 71, and the distal ends of which are linked to the distal tubular wall 36.

In the second stressed state, or low stress state, of the plurality of collapsible legs 70, as shown on FIGS. 8A and 9A, the drug delivery device 100 is in its luer lock connection position. In the collapsed state of the plurality of collapsible legs 70, corresponding to a higher stressed state of collapsible legs 70, as shown on FIGS. 8B and 9B, the drug delivery device 100 is in its luer slip connection position. Thanks to the elastic properties of the collapsible legs 70, the drug delivery device 100 is automatically moved back in its luer lock connection position when the proximal pressure exerted on the adaptor 30 is released.

The drug delivery device and the adaptor of the invention therefore allow changing connectors easily, quickly, and with no need for the user to reconfigure the drug delivery device between two successive connections, regardless of the type of connector that is used, in particular a luer lock connector or a luer slip connector.

The invention claimed is:

1. A drug delivery device comprising:
    a reservoir for containing a product, said reservoir having a distally projecting end-piece having a longitudinal axis A and defining an axial passageway for the transfer of the product from the reservoir, said end-piece having a distal portion,
    an adaptor having a collar having a flexible tab engageable around said end-piece so that said collar is axially movable with respect to said end-piece, said adaptor covering at least part of said end-piece, the adaptor having a distal tubular wall extending from said collar in the distal direction and surrounding at least part of said distal portion of said end-piece when said collar is engaged around said end-piece, said tubular wall having a thread on an inner wall,
    a securing structure for limiting the axial movement of said collar with respect to said end-piece once said collar is engaged around said end-piece, between a most distal position of said collar, in which a first length of said distal portion is left uncovered by said adaptor, and a most proximal position of said collar, in which a second length of said distal portion, greater than said first portion, is left uncovered by said adaptor, and
    a biasing element for urging said collar towards its most distal position, at least a portion of said biasing element being compressible along a longitudinal axis of the end piece.

2. The drug delivery device according to claim 1, wherein said securing structure comprises a proximal lock for preventing said collar from moving beyond its most proximal position and a distal lock for preventing said collar from moving beyond its most distal position.

3. The drug delivery device according to claim 2, wherein said proximal lock comprises a transversal wall of said reservoir.

4. The drug delivery device according to claim 2, wherein the distal lock comprises an annular ridge provided on an outer wall of said end-piece and an abutment surface provided on an inner wall of said collar, said abutment surface coming in engagement onto said annular ridge when said collar is urged in the distal direction once it is engaged around said end-piece.

5. The drug delivery device according to claim 1, wherein said biasing element comprises one or more flexible legs extending from said collar in the proximal direction, said flexible legs being in a first stressed state when said collar is in its most proximal position, said flexible legs being in a second stressed state when said collar is in its most distal position, said second stressed state being a state of lower stress than said first stressed state.

6. The drug delivery device according to claim 5, wherein said flexible legs are made of a material selected from olefins, polyamide, polycarbonate, polyetherketone and combinations thereof.

7. The drug delivery device according to claim 1, further comprising a protector for preventing access to the biasing element by a user.

8. The drug delivery device according to claim 7, wherein said protector comprises a proximal tubular wall extending from said collar in the proximal direction and surrounding said flexible legs.

9. The drug delivery device according to claim 1, further comprising an anti-rotation element for limiting rotation of said collar with respect to the end-piece once said collar is engaged with said end-piece.

10. The drug delivery device according to claim 9, wherein said anti-rotation element comprises one or more longitudinal ridges located on an outer wall of said end-piece, and one or more recesses located on an inner wall of said collar, said longitudinal ridges being engaged into said recesses and thereby preventing said collar from rotating with respect to said end-piece.

11. The drug delivery device according to claim 1, wherein said end-piece is made of glass.

12. The drug delivery device according to claim 1, wherein said end-piece is made of plastic.

13. The drug delivery device according to claim 1, wherein said distal portion is a male luer.

14. An adaptor for forming a drug delivery device, the adaptor comprising a collar having a flexible tab and the collar arranged for cooperating with a reservoir, the reservoir having a distally projecting end-piece having a longitudinal axis A and defining an axial passageway for a transfer of a product from the reservoir, the end-piece having a distal portion, the collar comprising a biasing element for urging said collar towards its most distal position when connected to said drug delivery device, the adaptor having a distal tubular wall extending from said collar in the distal direction and surrounding at least part of said distal portion of said end-piece when said collar is engaged around said end-piece, said tubular wall having a thread on an inner wall,
    wherein at least a portion of the biasing element is compressible along a longitudinal axis of the end piece.

15. The adaptor of claim 14, wherein said biasing element comprises one or more flexible legs extending from said collar in the proximal direction, said flexible legs adapted to be in a first stressed state when said collar is in its most proximal position, said flexible legs adapted to be in a second stressed state when said collar is in its most distal position, said second stressed state being a state of lower stress than said first stressed state.

16. The drug delivery device according to claim 1, wherein said biasing element comprises one or more helicoidal flexible legs extending from said collar in the proximal direction.

17. The adaptor of claim 14, wherein said biasing element comprises one or more helicoidal flexible legs extending from said collar in the proximal direction.

18. The adaptor of claim 14, the adaptor having a protector for preventing access to the biasing element by a user.

19. A drug delivery device comprising:
    a reservoir for containing a product, said reservoir having a distally projecting end-piece having a longitudinal axis A and defining an axial passageway for the transfer of the product from the reservoir, said end-piece having a distal portion, an adaptor having a collar engageable around said end-piece so that said collar is axially movable with respect to said end-piece, said adaptor covering at least part of said end-piece, the adaptor having a distal tubular wall extending from said collar in the distal direction and surrounding at least part of said distal portion of said end-piece when said collar is engaged around said end-piece, said tubular wall having a thread on an inner wall, a securing structure for limiting the axial movement of said collar with respect to said end-piece once said collar is engaged around said end-piece, between a most distal position of said collar, in which a first length of said distal portion is left uncovered by said adaptor, and a most proximal position of said collar, in which a second length of said distal portion, greater than said first portion, is left uncovered by said adaptor, and a biasing element for urging said collar towards its most distal position, at least a portion of said biasing element being compressible along a longitudinal axis of the end piece, wherein the distal portion is a male luer.

* * * * *